US006156212A

United States Patent [19]

Rader et al.

[11] Patent Number: 6,156,212
[45] Date of Patent: Dec. 5, 2000

[54] OPPOSED-FLOW VIRTUAL CYCLONE FOR PARTICLE CONCENTRATION

[75] Inventors: Daniel J. Rader, Lafayette, Calif.; John R. Torczynski, Albuquerque, N. Mex.

[73] Assignee: Sandia Corporation, Livermore, Calif.

[21] Appl. No.: 09/244,259

[22] Filed: Feb. 3, 1999

[51] Int. Cl.[7] .............................. B01D 21/26; G01N 1/00

[52] U.S. Cl. ................... 210/788; 210/512.1; 210/513.2; 55/428; 55/429; 55/459; 55/462; 73/28.05; 209/143; 209/715; 209/725; 356/38

[58] Field of Search ............................. 210/512.1, 512.2, 210/787, 788; 55/459.1, 428, 429, 430, 462, 510; 269/143, 715, 725; 356/38; 73/28.05

[56] References Cited

U.S. PATENT DOCUMENTS 4,942,297 11/1990 Johnson et al. .......................... 356/38
4,972,957 11/1990 Lu et al. ................................ 209/143

*Primary Examiner*—David A. Reifsnyder
*Attorney, Agent, or Firm*—Lafayette Carnahan

[57] ABSTRACT

An opposed-flow virtual cyclone for aerosol collation which can accurately collect, classify, and concentrate (enrich) particles in a specific size range. The opposed-flow virtual cyclone is a variation on the virtual cyclone and has its inherent advantages (no-impact particle separation in a simple geometry), while providing a more robust design for concentrating particles in a flow-through type system. The opposed-flow virtual cyclone consists of two geometrically similar virtual cyclones arranged such that their inlet jets are inwardly directed and symmetrically opposed relative to a plane of symmetry located between the two inlet slits. A top plate bounds both jets on the “top” side of the inlets, while the other or lower wall curves “down” and away from each inlet jet. Each inlet jet will follow the adjacent lower wall as it turns away, and that particles will be transferred away from the wall and towards the symmetry plane by centrifugal action. After turning, the two jets merge smoothly along the symmetry line and flow parallel to it through the throat. Particles are transferred from the main flows, across a dividing streamline, and into a central recirculating region, where particle concentrations become greatly increased relative to the main stream.

22 Claims, 4 Drawing Sheets

OPPOSED-FLOW VIRTUAL CYCLONE FOR PARTICLE CONCENTRATION

The United States Government has rights in this invention pursuant to Contract No. DE-AC04-94AL 85000 between the United States Department of Energy and the Sandia Corporation for the operation of the Sandia National Laboratories.

BACKGROUND OF THE INVENTION

The present invention relates to particle separation, particularly to collecting particles for subsequent characterization or analysis, and more particularly to an opposed-flow virtual cyclone which accurately collects, classifies, and concentrates (enriches) particles in a specific size range.

Particle separation, characterization, and/or analysis has involved continuous research and development for many decades. However, more recently, substantial interest has been directed to collection and analysis of air-borne particles, referred to as aerosol collectors. As used here, the term aerosol refers to liquid or solid particles which are suspended in a gas (e.g., air). The particles may be anthropogenic (such as smog, fly-ash, or smoke) or naturally occurring (such as pollens, dust, or mists). One problem facing the aerosol field is that of collecting the particles for subsequent characterization or analysis. Although some characterization of these air-borne particles can be performed in situ, in many cases it is essential to deposit these particles onto a solid substrate, or to inject them into a liquid for the purpose of detailed physical or chemical analysis. Consequently, a large number of aerosol collectors have been developed in the past, including devices such as jet impingers, jet impactors, and filters.

In many cases it is desirable to sort the particles according to size as part of the collection process, such as to determine the aerosol size distribution (mass of suspended particles as a function of particle size per volume of gas) or to identify any size-related dependencies of particle chemical characteristics. A large number of aerosol collectors with size-classification capabilities appear in the prior art, including cascade inertial impactors, cyclones, and inertial spectrometers. The aerosol collection task is further complicated when particles in a specific size interval or range are of interest, especially when the concentration of these particles is very low (where particle concentration is given by the number of particles per unit volume of gas).

Of particular interest is the example of bioaerosols, which includes air-borne pollens, viruses, or bacteria. Bioaerosols can result from natural processes (pollen releases by plants), or from human activities by inadvertent (e.g., in operating rooms, communicable diseases) or intentional (agricultural or battlefield) releases. The concentration of bioaerosols can be quite low, and the challenge in their analysis is to separate them from a potentially high concentration of background aerosol. For many aerosol collection problems, including bioaerosols, the ideal collector would be one which accurately collects, classifies, and concentrates (enriches) particles in a specific size range.

One prior approach to aerosol enrichment is the aerodynamic lens, schematically illustrated in FIG. 1, which concentrates particles along the centerline of an axisymmetric geometry through a series of flow contractions and enlargements. See Peng et al., Aerosol Sci. Technol. 22:293–313 and 314–325, 1995. After each contraction, particles are moved closer to the centerline if their aerodynamic sizes are less than a critical size, while particles larger than the critical size more further from the centerline. Through a careful design of a series of lenses, particle enrichment within a specific size range can be achieved. However, there are several drawbacks to the aerodynamic lens, including: 1) complexity in design, construction, and alignment of a multi-lens system, 2) difficulties in getting high enrichments over a wide size range, and 3) particle deposition and build-up on walls of the lens.

Another prior means of achieving particle enrichment is the virtual impactor, schematically shown in FIG. 2, and which generally consists of an axisymrnetric jet impinging on a normal plate which has a small hole (perhaps leading to a cavity below) in it located at the jet centerline. See Marple et al., Environ. Sci. Technol., 14:976–985, 1980. If flow through the hole is restricted, then the region behind the hole becomes a stagnation zone, which acts as a "virtual surface." Thus, the impinging jet is deflected by the plate (and the virtual surface at its center) and flows radially outward. Because of their inertia, particles cannot make the turn and are impacted into the virtual surface, leading to particle enrichment in the cavity below. By careful design of a series of vertical impactor stages, particle enrichment in a specific size range can be achieved. However, the virtual impactor suffers many of the same drawbacks as the aerodynamic lens: 1) complexity in design, construction, and alignment, 2) difficulties in getting high enrichments over a wide size range, and 3) particle deposition and build-up on walls.

Recently, a virtual cyclone, schematically illustrated in FIGS. 3A and 3B, was developed as a means of separating particles form a main flow and concentrating them in an adjacent recirculating chamber. See Torczynski and Rader, "The Virtual Cyclone: A Device for Nonimpact Particle Separation", Aerosol Sci. Technol., 26:560–573, 1997. In the virtual cyclone, the main particle-laden flow follows a wall that curves away from the original flow direction. Although a wall forms the inner boundary of the main flow, its outer boundary is formed by an adjacent flow, often a confined recirculating flow, into which particles are transferred by centrifugal action. Thus, in the virtual cyclone, particles are separated from the main flow by crossing a dividing streamline that separates the main flow stream from an adjacent flow stream. If a confined recirculating chamber geometry is used, particle concentrations in the recirculating region can be greatly increased relative to the main stream. A primary advantage of the virtual cyclone is that it accomplishes inertial separation in such a way as to greatly reduce particle deposition on walls.

However, experiments have shown that turbulent mixing produced by shear-layer roll-up can limit particle-concentration enhancement at high flow Reynolds numbers. In addition, removing particles from the recirculating chamber for analysis presents some challenge in the virtual cyclone geometry. Thus, the need persists for a device which accurately collects, classifies, and concentrates (enriches) particles of interest.

The present invention provides a solution to the above-mentioned need by providing an opposed-flow virtual cyclone, which is a variation on the above-referenced virtual cyclone in that it preserves its inherent advantages (no-impact particle separation in a simple geometry), while providing a more robust design for concentrating particles in a flow-through type system. In simplest terms, the opposed-flow virtual cyclone of the present invention consists of two geometrically similar virtual cyclones arranged such that their inlet jets are inwardly directed and symmetrically opposed relative to a plane of symmetry located midway between the two inlets. As in the virtual cyclone, each inlet jet will follow the adjacent curved wall as it turns away and that particles will be transferred away from the curved wall and towards the symmetry plane by centrifugal action. After turning, the two jets merge smoothly along the symmetry line and flow parallel to it. The particles are transferred from the main flows, across the dividing streamline, and into the central recirculating region, where particle concentrations become greatly increased relative to the main flow. Thus, the present invention provides a device which is able to accurately collect, classify, and concentrate (enrich) particles of interest.

SUMMARY OF THE INVENTION

It is an object of the present invention to provide a particle separation device capable of particle concentration in a flow-through system.

A further object of the invention is to provide a device for separating particles of interest by no-impact particle separation and thus minimize deposition of particles on the wall surfaces of the device.

A further object of the invention is to provide a particle separation device utilizing opposed inlet fluid flows which pass through a device having walls which curve away from the original fluid flow direction, whereby the opposed fluid flows follow the curved walls and merge smoothly together such that particles in the fluid flow concentrate in the central section of the merged fluid flows. Another object of the invention is to provide an opposed-flow virtual cyclone for particle concentration.

Figure 3A:
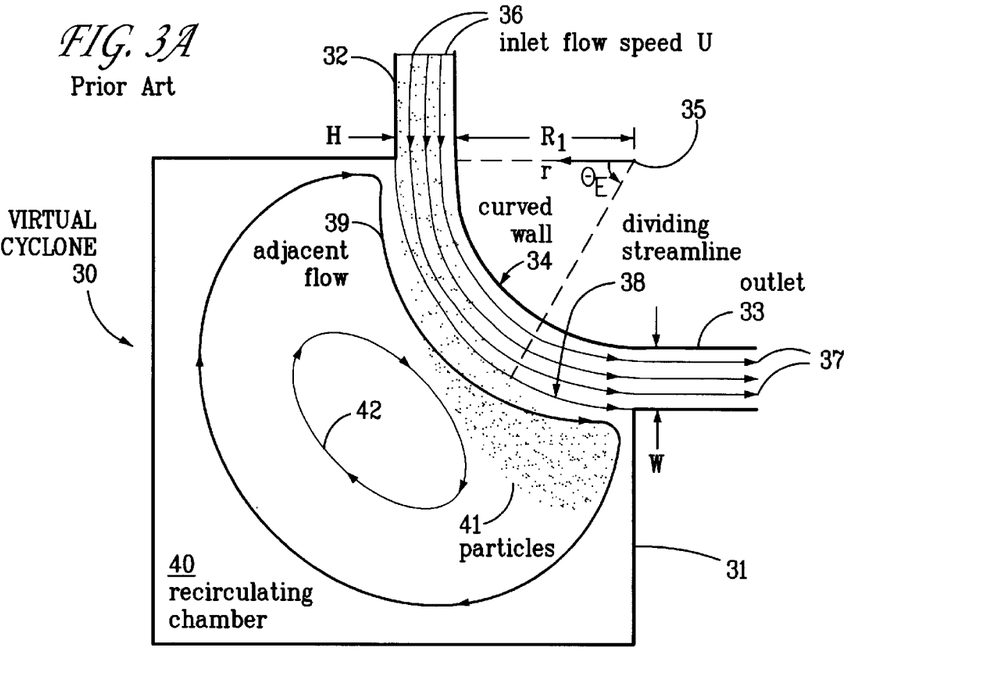
Figure 3B:
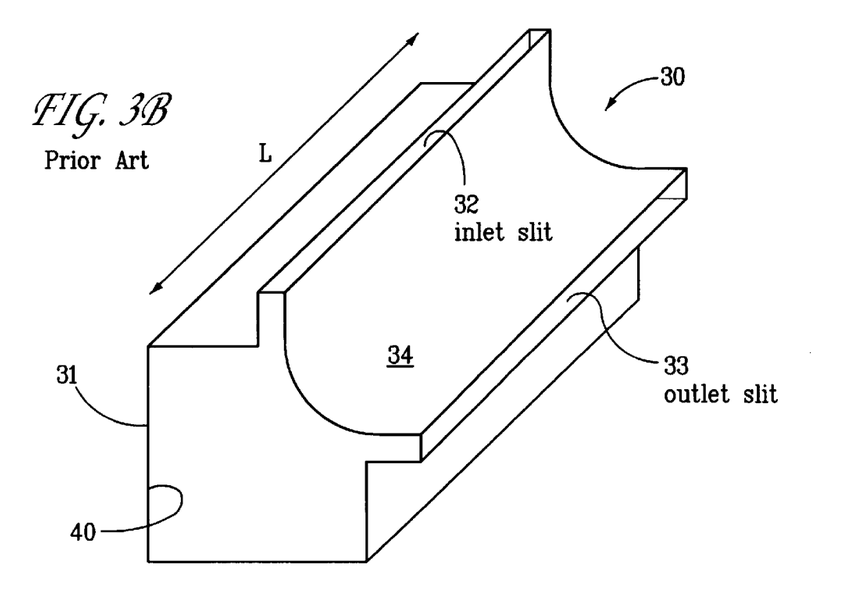

Another object of the invention is to provide a particle separation/concentration device utilizing a pair of virtual cyclones positioned in an opposed flow arrangement, which provides the advantages of the virtual cyclone while eliminating the disadvantages thereof.

Another object of the invention is to provide an opposed-flow virtual cyclone which accurately collects, classifies, and concentrates particles of interest.

Another object of the invention is to provide an opposed-flow virtual cyclone capable of concentrating in at least the 1–5$\mu$ diameter range without particle impact separation.

Other objects and advantages of the present invention will become apparent from the following description and accompanying drawings. The invention is an opposed-flow virtual cyclone for concentrating particles in an aerosol flow. The opposed-flow virtual cyclone utilizes the advantages, without the disadvantages, of the known virtual cyclone; namely, the no-impact separation in a simple geometry, without turbulent mixing produced by shear-layer roll-up which limits particle concentration enhancements at high flow Reynolds numbers. Basically, the present invention utilizes opposed inlet fluid flows into a housing having an upper flat wall and curved lower walls which terminate in a throat or opening therebetween. The opposed fluid flows follow the curved lower walls and particles are transferred away from the walls and towards the symmetry plane of the throat or opening in the housing by centrifugal action. After turning, the fluid flows merge smoothly along the symmetry line and flow parallel to it through the throat. A recirculation region is formed between the two fluid flows, about the symmetry plane, below the upper flat wall, and above the point at which the fluid flows merge. Thus, the particles are transferred from the main flows, across a dividing streamline, and into the central recirculating region, where particle concentrations become greatly increased relative to the main stream. The particles will leak out of the recirculation zone, and these particles are highly focused into a narrow region about the symmetry plane between the convening fluid flows, and can, for example, be collected in a virtual impactor, such as shown in FIG. 2, wherein the throat of the housing functions as part of the impactor.

BRIEF DESCRIPTION OF THE DRAWINGS

The accompanying drawings, which are incorporated into and form a part of the disclosure, illustrate an embodiment of the invention and, together with the description, serve to explain the principles of the invention.

FIG. 1 is a partial cross-sectional view of a prior art aerodynamic lens.

FIG. 2 is a cross-sectional view of a prior art virtual impactor.

FIG. 3A schematically illustrates in cross-section a side view of a prior art virtual cyclone.

FIG. 3B is a perspective view of the prior art virtual cyclone of FIG. 3A.

FIG. 4 is a schematic cross-sectional view of an embodiment of an opposed-flow virtual cyclone made in accordance with the present invention.

FIGS. 5A–5D illustrate numerical finite-element flow simulations performed to test the validity of the embodiment of the invention shown in FIG. 4.

DETAILED DESCRIPTION OF THE INVENTION

The present invention is directed to an opposed-flow virtual cyclone for particle concentration. The invention is particularly applicable in the aerosol field, including bioaerosols, for accurately collecting, classifying, and concentrating (enriching) particles of interest, such as particles in the 1–5 $\mu$m diameter range.

As pointed out above, the present invention provides a significant advance over the aerodynamic lens indicated generally at 10 in FIG. 1 and comprises a member 11, only partially shown, having an inward protruding section 12 which functions to produce a flow contraction toward the axis or centerline 13 of member 11 as indicated by the fluid streamline arrow 14 and the particle trajectory arrow 15, whereby particles are moved closer to the axis or centerline 13. Also, as pointed out above, the present invention provides an advance over the virtual impactor of FIG. 2, although it may include a virtual impactor section. As seen in FIG. 2, the impactor 20 comprises a member 21 having an opening 22 extending therethrough with a tapered entrance section 23, with member 21 being spaced from a plate or member 23 having an opening 24 and a counter-sink 25 having a collector 26 therein. The space between members 21 and 23 define outlet passageways 27. A fluid flow through the member 21 produces a fluid streamline indicated by arrow 28 and a particle track indicated by arrow 29, wherein the fluid streamline 28 strikes the surface of plate or member 23 and passes outwardly via passageways 27. The centrally located particle track 29 passes through the opening 24 in plate 23 into collector 26.

As pointed out above, the aerodynamic lens and the virtual impactor of FIGS. 1 and 2 are effective to a certain extent in concentrating particles of the size of interest, but have disadvantages which were overcome by the virtual cyclone illustrated in FIGS. 3A and 3B which provided a means of separating particles from a main flow and concentrating them in an adjacent recirculating chamber. The embodiment of a virtual cyclone as shown in FIGS. 3A and 3B is generally indicated at 30 having a housing 31 protruding inlet slit section 32 and a protruding outlet slit section 33 located about 90° from the inlet slit section 32 and which are interconnected via a curved wall section 34. The housing 31 has a length L, with the inlet slit section 32 having a width H and the outlet slit section 33 having a width W. The curvature of wall section 34 is determined by a radius, r, from a point 35 having a distance $R_1$ from inlet slit section 32 which passes through an angle $\theta_E$. As seen in FIG. 3A a fluid flow indicated by arrows 36 enters inlet slit section 32 having an inlet flow speed U and passes through housing 31 along the curved wall section 34 and passes outwardly from housing 31 via outlet slit section 33 as indicated by arrows 37. As seen, while curved wall section 34 forms the inner boundary of the main flow, indicated by arrows 36–37, through housing 31, its outer boundary, indicated by the dividing streamline 38, is formed by an adjacent flow indicated by arrow 39, a confined recirculating flow within a recirculating chamber section 40 of housing 31. Particles, indicated at 41, contained in the fluid flow (main flow 36–37) are transferred by centrifugal action by crossing the dividing streamline 38 and into the adjacent flow 39, and are then circulated, as indicated by arrow 42, within recirculating chamber section 40, wherein particle concentrations in the recirculating region of chamber 40 are greatly increased (enhanced) relative to the main steam (arrows 36–37).

The primary advantage of the virtual cyclone, as pointed out above, is that it accomplishes inertial separation in such a way as to greatly reduce particle deposition on walls, since the main particle-laden flow follows a curvature away from the original flow direction and the particles continue in the original flow direction and therefor are not deposited on the wall creating curvature of the main flow, as clearly seen in FIG. 3A.

The present invention preserves the inherent advantages of the virtual cyclone of FIGS. 3A–3B; namely, no-impact particle separation in a simple geometry, while providing a more robust design for concentrating particles in a flow-through type system, while eliminating the turbulent mixing in the known virtual cyclone, produced by shear-layer roll-up, which limits particle-concentration enhancements at high flow Reynolds numbers. This is accomplished with an opposed-flow virtual cyclone, basically composed of two geometrically similar virtual cyclones arranged such that their inlet jets or fluid flows are inwardly directed and symmetrically opposed relative to a plane of symmetry located midway between the two inlet slits through which the inlet jets pass. Thus, the present invention provides a device which accurately collects, classifies, and concentrates (enriches) particles of interest. Alternately, an axisymmetric arrangement may be utilized. Also, the present invention may be utilized with fluids of either the liquid or gaseous type.

Based on numerical simulations (using the commercial flow solver FIDAP, Fluent International) several 2-D geometries have been shown to provide significant particle enrichment along the plane of symmetry for particles in the 1 to 5 micron diameter range. This size range is of particular interest to bioaerosol detector applications, although other size ranges are achievable by modification to the opposed-flow virtual cyclone geometry or operating conditions.

Figure 4:
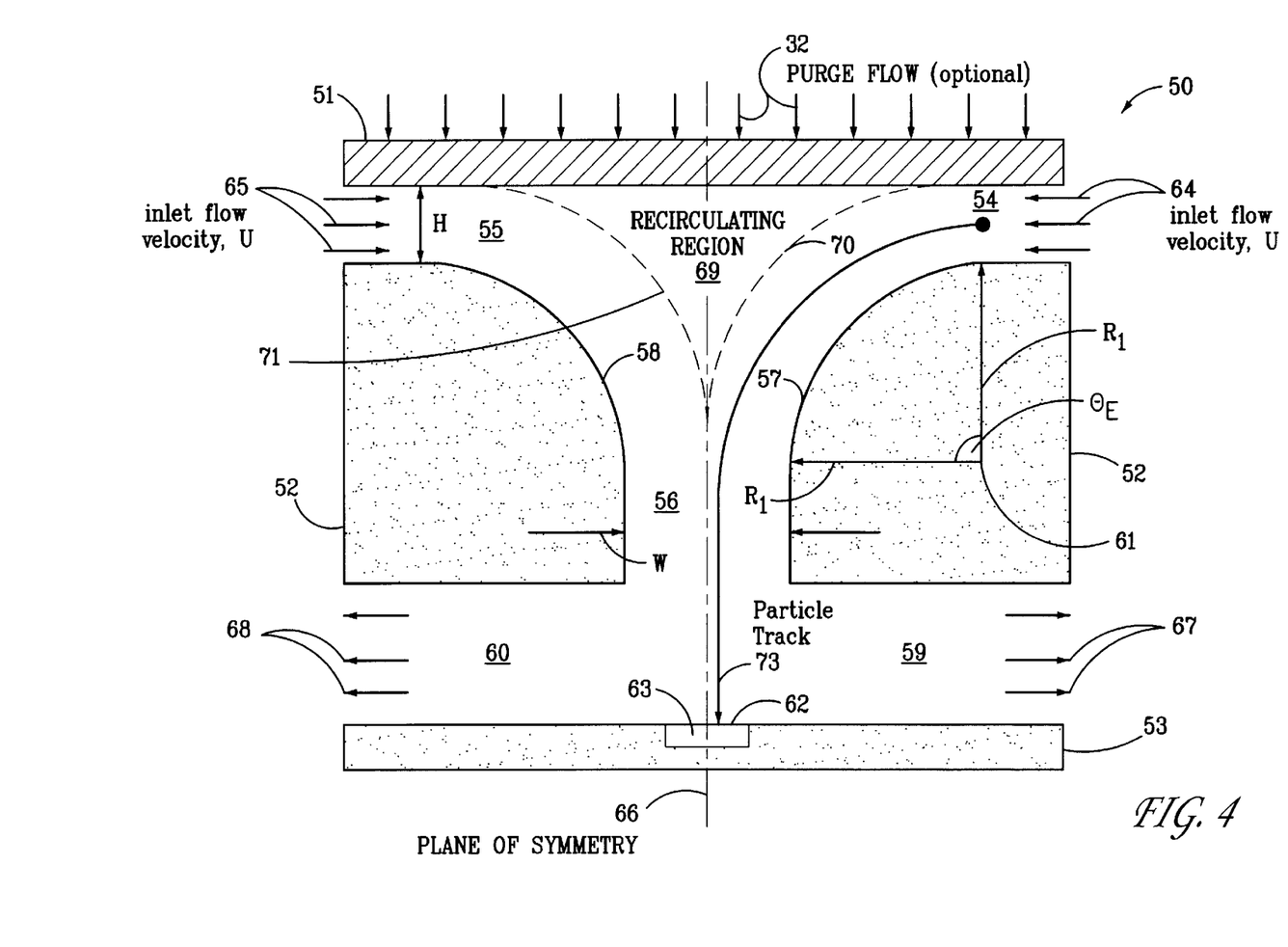

Referring now to FIG. 4, which illustrates schematically an embodiment of an opposed-flow virtual cyclone (OFVC), indicated generally at 50, and comprising a top plate or member 51, a housing or member 52 and a bottom plate or member 53. However, the OFVC in actuality only comprises the top plate 51 and an upper section of housing 52 in that the lower section of housing 52 and bottom plate 53 define a collector mechanism and other types of collectors may be used. The housing 52 is spaced from top plate 51 to define fluid inlets 54 and 55 and includes a central opening or throat 56 which communicates with fluid inlets 54 and 55 via curved wall sections 57 and 58. Bottom plate 53 is spaced from housing 52 to define fluid outlets 59 and 60. The fluid inlets 54 and 55 have an initial width of H with the central opening or throat 56 having a final width W, with the curve of wall sections 57 and 58 having a radius $R_1$ and an curvature angle of $\theta_E$ about a point 61. Top plate 51 is solid, but may be porous, as described hereinafter relative to a modified embodiment. Bottom plate 53 includes an opening 62 behind which is a collector cavity 63. Inlet fluid flows or inlet jets, indicated by arrows 64 and 65, having a velocity U, pass through fluid inlets 54 and 55 from opposite directions, and as described above with respect to the virtual cyclone of FIGS. 3A–3B follow the curved wall sections 57 and 58, and then smoothly merge together in the central opening or throat 56, and particles therein will be transferred away from the curved wall sections 57 and 58 and towards a symmetry plane 66 by centrifugal action. After turning and smoothly merging together the two inlet jets flow along a path parallel to the symmetry line 66 and through the throat or central opening 56, and outwardly through fluid outlets 59 and 60, as indicated by arrows 67 and 68. With a solid top plate 51, a central recirculation region indicated at 69 is formed between the two inlet flows or jets (i.e., about the symmetry plane 66, below the top plate 51, and above the point at which the two jets merge in opening 56). Thus, in this embodiment of the OFVC, particles are transferred from the main or jet flows, across dividing streamlines 70 and 71, and into the central recirculating region 69, where particle concentrations become greatly increased relative to the main or jet flows 64 and 65. Eventually, the particles will leak out of the recirculation region, and these particles will be highly focused into a narrow region about the symmetry plane 66 between the two converging flows 64 and 65 and, for example, strike the opening 62 for collection in the cavity 63.

If the top plate 51 was composed of porous material, a small fluid or purge flow as indicated by arrows 72 would be provided through the porous top plate for the purpose of purging particles from the recirculating region 69, and would provide particle enrichment along the symmetry plane 66 in a flow-through geometry, producing a flow-through particle track indicated by arrow 73, shown only on one side. This approach, porous top plate, would eliminate the time delay inherent before particles begin to leak out of the recirculation region 69 when a solid top plate is used.

Another modification of the embodiments of the OFVC would involve varying the shape of the curved wall sections 57 and 58 used to turn the flow. As shown in FIG. 4, the curved wall sections 57 and 58 are semicircular. For example, the smooth curved surfaces shown in FIG. 4 would be changed to a sharp-edged wall section configuration so that the flow path from fluid inlets 54 and 55 to central opening or throat 56 would have a "T" configuration. However, while calculations have shown that the "T" geometry does concentrate particles about the symmetry plane, the performance is not as good as in the preferred OFVC configuration illustrated in FIG. 4 because: 1) the recirculation region between the opposed incoming fluid jets is lost, so that less room is available for particles to slow down, and 2) unwanted recirculation regions can form downstream of the sharp-edged lips of the incoming jet flows, which could destabilize the flow and lead to wall losses.

Figure 1:
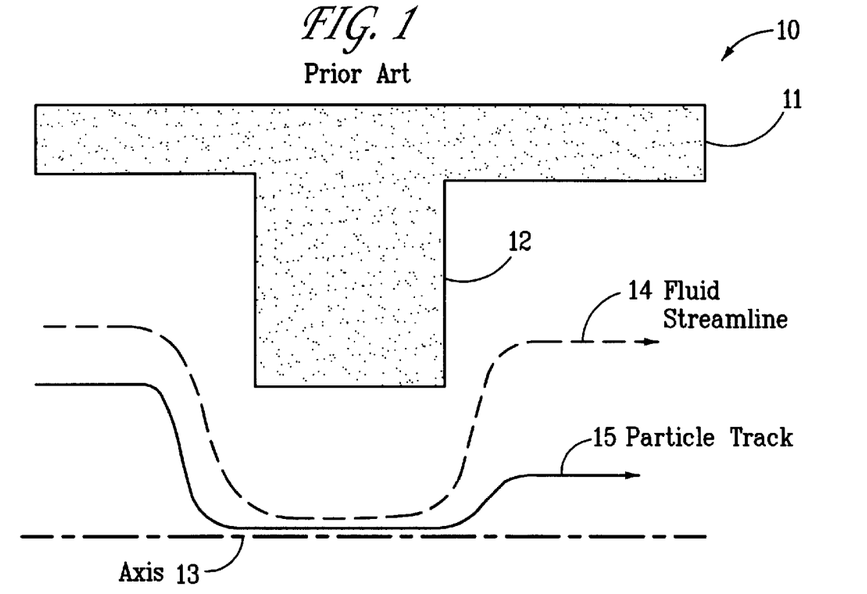
Figure 2:
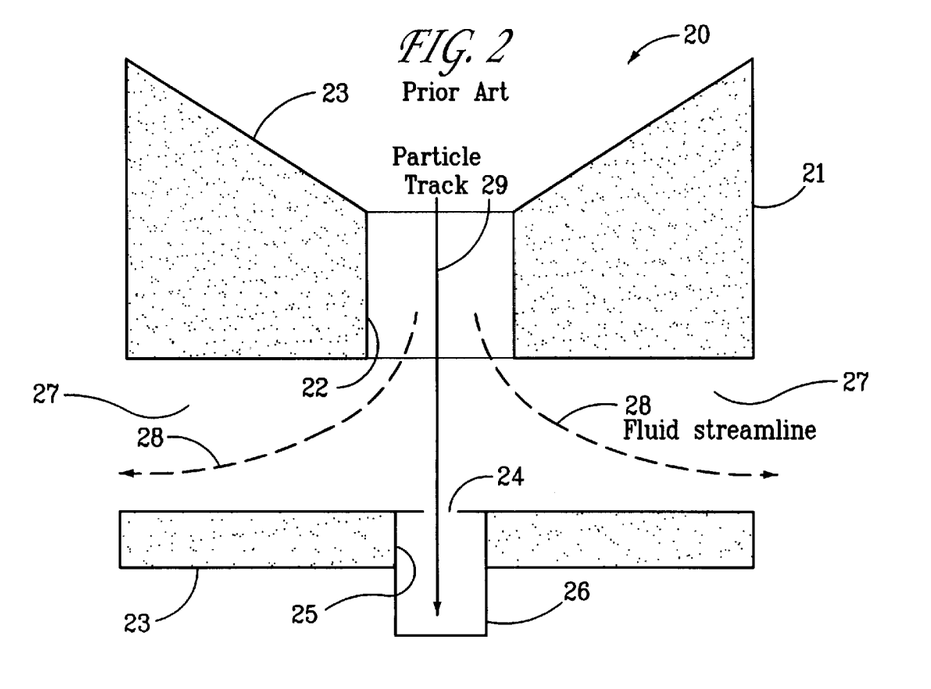

As pointed out above, the OFVC of FIG. 4 ends at the point in the throat or central opening 56 where the inlet jets or flows 64 and 65 merge and where the exiting particles are concentrated in a narrow region about the flow plane of symmetry 66. A variety of other options for collecting the particles downstream from that point are available. For example, the exiting jet could impinge on a normal plate such as a traditional impactor, with significant advantage that the particle deposit on the plate will be highly concentrated about the symmetry plane. Another variation would be an improved impinger, achieved by placing a small pool of liquid in the cavity 63 of the plate 53 in FIG. 4 to receive the particles for later analysis. Also, an improved virtual impactor, similar to FIG. 2 could also be constructed in the bottom plate 53 of FIG. 4 by forming a collection cavity along the plane of symmetry 66 and, attached to the plate, and in communication with the opening 62, whereby the particle-enriched flow at the symmetry plane is collected.

Initial verification modeling has shown that both 2-D and axisymmetric variations of the OFVC give the same qualitative result of inertially focusing particles along the symmetry lane. Based on numerical simulations described below, however, it appears that the 2-D geometries studied to date offer better performance than the axisymmetric geometries which were considered. Thus, the following description will focus on a 2-D implementation, which is theoretically infinite in extent in the third (z) direction, the length L (not shown) in the FIG. 4 embodiment. In particular terms, the 2-D assumption requires that the length in the z-direction, L, be much longer than the characteristic lengths in the x-y plane, the widths H and W of FIG. 4, i.e., L>>W and L>>H. Edge (or 3-D) effects are expected to become important for L~W, but these have not been yet considered. Although the following 2-D geometries appear to be preferred embodiments based on a limited number of numerical simulations, the present invention is not intended to be so restricted, but allows for other 2-D, 3-D, or axisymmetric geometries which could be made to function in the same manner.

Generally, the OFVC will concentrate particles only within a particular size range. If particles are to small, they will tend to follow the main flow instead of being centrifuged across the dividing streamline. If particles are too large, they will overshoot the recirculating region and pass into the opposing jet, and thereby resist focusing. Actually, the fact that the OFVC will only concentrate particles within a particular size range can be used to advantage, e.g., in bioaerosol sampling it is desirable to only collect particles with diameters between about one and five microns. An approximate operating size range for the OFVC can be determined based on flow conditions and geometric parameters. These design equations are shown here.

Minimum collected size: An approximate expression for the minimum-size particle that can be effectively separated from the main flow in a standard virtual cyclone has been given in terms of the particle Stokes number:

$$St_{\min} = \frac{\tau_{\min} U}{H} \approx \frac{1}{\theta_E} \quad (1)$$

where U is the inlet gas velocity, H is the inlet width, $\theta_E$ is the total angel that the main flows turn through (=π/2 for the OFVC shown in FIG. 4), and $\tau_{min}$ is the characteristic particle relaxation time (a measure of how fast a particle can adjust or relax its velocity to a new condition of forces) corresponding to the minimum-size particle to be collected:

$$\tau_{\min} = \frac{C_{slip} \rho_p d_{p,\min}^2}{18\mu} \quad (2)$$

where $C_{slip}$ is a factor that corrects for particle noncontinuum drag ($C_{slip}$~1 for particles larger than about one micron at atmospheric conditions), $\rho_p$ and $d_{p,min}$ are the particle density and diameter, respectively, and $\mu$ is the gas viscosity. Equation (1) links virtual cyclone parameters to particle parameters, an it can be combined with Equation (2) to give the following expression for the minimum size particle that can be completely separated from the main flow in a virtual cyclone:

$$d_{p,\min} = \sqrt{\frac{18\mu}{C_{slip}\rho_p} \cdot \frac{H}{U\theta_E}} = \sqrt{\frac{36\mu}{\pi C_{slip}\rho_p} \cdot \frac{H}{U}} \quad (3)$$

where the final equality is for the case $\theta_E$=π/2 shown in FIG. 4. Based on Equation (3), it can be seen that smaller particles can be separated from the main flow (i.e., concentrated about the centerline) by decreasing the inlet slit width, or by increasing the inlet gas velocity or the turning angle. This has interesting implications for micromachined devices, which could be used to separate very small sizes by fabrication of very thin slits. Note that pressure and gas dependencies are buried within the slip factor, and that smaller-sized particles could be collected by operating at low pressures.

The derivation leading to Equation (3) is approximate, and neglects the fact that some fraction of particles smaller than $d_{p,min}$ will in fact be separated from the main flow. Equation (3) is intended for design purposes.

As mentioned above, if particles are too large, they will overshoot the recirculating region and pass into the opposing jet, and possibly resist focusing. One way to control the over-shoot phenomenon is to make the recirculating region large enough to allow incoming large particles a sufficient distance to slow down. As a guide in determining what distance is needed, consider the distance a particle travels before stopping (the so-called stopping distance) if injected into a quiescent gas at the jet inlet velocity U:

$$S = \tau U = \frac{C_{slip}\rho_p d_p^2 U}{18\mu}. \quad (4)$$

For successful particle concentration, the incoming particles should not overshoot the symmetry plane, and therefore it is suggested that the stopping distance for the largest particle which is to be collected, $S_{max}$, should equal approximately the distance between the inlet and symmetry plane. For the geometry shown in FIG. 4, this approximation would give:

$$S_{\max} = \tau_{\max} U \approx R_1 + \frac{W}{2} \quad (5)$$

where $R_1$ is the radius of curvature of the wall which turns the flow (see FIG. 4) and where $\tau_{max}$ is the characteristic particle relaxation time corresponding to the maximum-sized particle ($\tau_{max}$ can be calculated just as in Equation (2) with $d_{p,min}$ replaced by $d_{p,max}$). Numerical simulations have shown that one successful geometry is that for which the throat width is approximately twice the inlet slit width, or W~2H. For this embodiment, and combining Equation (5)

with Equation (4), the following expression is obtained for the maximum size particle that can be concentrated in an OFVC:

$$d_{p,max} = \sqrt{\frac{18\mu}{C_{slip}\rho_p} \cdot \frac{R_1 + W/2}{U}} \approx \sqrt{\frac{18\mu}{C_{slip}\rho_p} \cdot \frac{R_1 + H}{U}}. \quad (6)$$

Based on Equation (6), it can be seen that the high-end of the particle concentrating range can be increased by increasing the inlet slit width or the turning-wall radius of curvature, or by decreasing the inlet gas velocity.

Design Considerations: The OFVC affords a great deal of flexibility in designing for a specific particle size range. For example, to design an OFVC system (such as shown in FIG. 4 with W=2H and $\theta_E=\pi/2$) for a specific particle size range, $d_{p,min}$ can be obtained by the proper choice of H/U based on Equation (3), and $d_{p,max}$ can be obtained by the proper choice of $R_1/U$ based on Equation (6). Numerical simulations of this 2-D geometry showed that the parameters H and $R_1$ were in fact independent over the limited parameter space investigated.

One challenge of the OFVC is to concentrate particles down to and below about $1\mu$. As shown in Equations (3) and (6), small-sized particle operation is achieved by operating at very high inlet velocities. In some design scenarios, however, the value of the inlet velocity will be limited on the high end by pressure drop requirements. Given that the pressure drop and velocity are approximately related by $\Delta P \sim \rho U^2/2$, where $\rho$ is the gas density, the desired inlet velocity is then set by the maximum allowable pressure drop:

$$U \leq \sqrt{\frac{2\Delta P_{max}}{\rho}} \quad (7)$$

As an example, consider the design of an OFVC that must operate with air at atmospheric conditions with a maximum pressure drop $\Delta P_{max}$. To avoid necessarily small physical dimensions, the device should be operated at as high a velocity as possible, so that U is given by Equation (7) with the quality sign (note that the resulting calculated velocity must certainly be less than the speed of sound, and should not be so large as to raise compressibility concerns). For this example, consider the 2-D OFVC shown in FIG. 4 with W=2H, and $\theta_E=\pi/2$. Using Equation (2), the size requirements $d_{p,min}$ and $d_{p,max}$ can be translated into relaxation time $\tau_{min}$ and $\tau_{max}$, respectively. Equation (1) then uniquely determines the inlet gap H, Equation (5) then uniquely determines $R_1$ (making use of the fact that W=2H), and the design is complete.

Table 1 below sets forth examples of possible OFVC designs to concentrate/collect particles in the 1.5 to 5 $\mu$m range for various gas inlet velocities (based on the 2-D OFVC geometry shown in FIG. 4).

TABLE 1

| U (m/s) | ~ΔP (torr) | H (mm) | W (mm) | R$_1$ (mm) | Q/L (lpm/cm) |
|---|---|---|---|---|---|
| 10 | 0.45 | 0.12 | 0.24 | 0.67 | 1.44 |
| 20 | 1.81 | 0.24 | 0.48 | 1.34 | 5.76 |
| 50 | 11.3 | 0.60 | 1.2 | 3.36 | 36.0 |
| 100 | 45.1 | 1.2 | 2.4 | 6.71 | 144. |

Some numerical examples are given Table 1 for some typical velocities/pressures of interest for collecting/concentrating a bioaerosol (of particle density 1 g/cm$^3$) in the size range of 1.5 to 5.0 $\mu$m. The flow rate per unit length of collector, Q/L, is found from the relation Q=2UHL where the factor of two is needed as there are two inlet slits. As seen in the table, operation at low pressure drop requires very small slit widths. Typically, the highest velocity at which compressibility effects can be ignored is U=100 m/s; at this velocity the required size range can be concentrated with a slit width slightly larger than a millimeter.

Figure 5A:
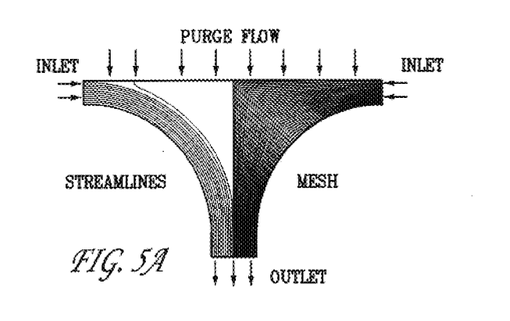
Figure 5B:
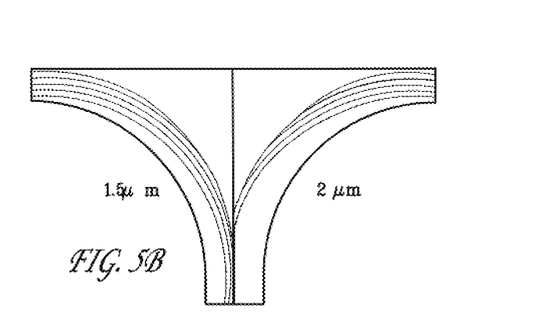
Figure 5C:
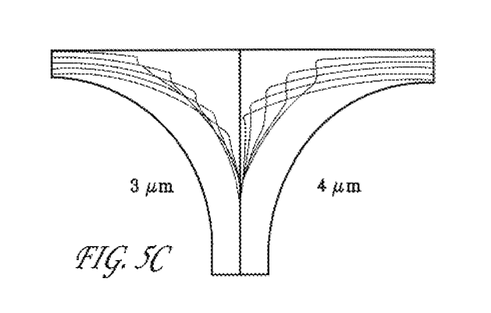
Figure 5D:
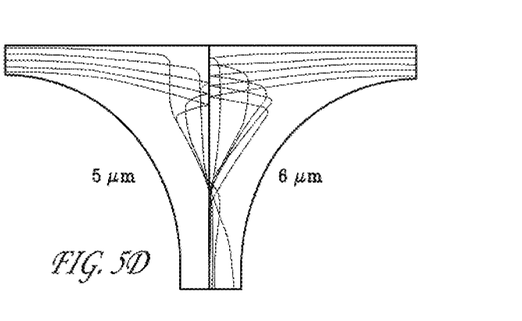

Simulations: Numerical finite-element flow simulations were performed to test the validity of the OFVC concept and the above design equations. The design goal for this example was to collect/concentrate a bioaerosol (of particle density 1 g/cm$^3$) in the size range from 1.5 to 5.0 $\mu$m with a low pressure drop. Consequently, the following conditions from Table 1 were assumed for these calculations: U=50 m/s, H=0.6 mm, W=1.2 mm, and $R_1$=3.5 mm. Note that to avoid a large recirculation flow from developing, a small flow was introduced through a porous top plate with a purge velocity of 0.5 m/s. The simulation results are exemplified by the curves shown in FIGS. 5A, 5B, 5C, and 5D. Note that because of the symmetry, each of the four plots are used to show two results, one on the left-hand side and one on the right-hand side. As shown in FIG. 5A (left side), the calculated fluid streamlines stay attached to the lower wall as it turns away, just as in the calculations for the standard virtual cyclone. Particle trajectories are shown in FIGS. 5B, 5C, and 5D: note that particle trajectories which cross the symmetry plane are specularly reflected back so that the entire path can be shown one side of the plot. The particle behavior was found to be in very good agreement with the above design guidelines: 1.5 $\mu$m particles showed moderate focusing, particles between 2 and 5 $\mu$m showed excellent focusing, and focusing was lost for particles larger than about 5 $\mu$m. As shown, the extent of particle focusing along the symmetry plane is very high in the particle size range 1.5 to 5 $\mu$m.

The device of the present invention is quite different from existing technology since it builds on the concept of the virtual cyclone, which was only developed in the last few years. A key discriminating feature of the virtual cyclone, and consequently the opposed-flow virtual cyclone as well, is that it performs inertial separation by turning a flow with a wall that curves away from the original direction rather than curving into the original direction, such as in a cyclone or impactor. As a consequence, particles are driven by inertia away from the wall, and so the chances of particles impacting on the wall are nearly removed.

The opposed-flow virtual cyclone (OFVC) of the present invention offers the following advantage over the aerodynamic lens and the virtual impactor (the primary competing technologies): 1) very low wall deposition for the particle size range of interest, 2) simpler geometry, i.e., easier manufacture and alignment than multistage devices, 3) high particle enrichment in a specific size range, 4) low pressure drop. The OFVC is very similar in operation to a standard virtual cyclone, but has the following advantages: 1) particle enrichment in a particular size range, 2) ease of operation in a flow-through mode using top-plate purge flow, and 3) appears to have more stable operation (this latter feature has not been proved experimentally). As noted above the present invention may be used for either liquid or gaseous flows.

While a particular embodiment of the invention with modifications thereof has been illustrated and described, along with various parameters, configurations, etc., such are not intended to be limiting. Modifications and changes may become apparent to those skilled in the art, and it is intended that the invention be limited only by the scope of the appended claims.

The invention claimed is:

1. An opposed-flow virtual cyclone for particle concentration and/or enrichment, comprising:
   means for forming a plurality of opposed fluid inlets, and
   means for forming a fluid outlet,
      said fluid outlet being formed transverse to and in fluid communication with said plurality of opposed fluid inlets.

2. The opposed-flow virtual cyclone of claim 1, wherein said means for forming a fluid outlet comprises a housing having an opening extending therethrough, said housing having curved surfaces adjacent to said opposed fluid inlets.

3. The opposed-flow virtual cyclone of claim 2, wherein said means for forming opposed fluid inlets includes said housing and a plate positioned in spaced relation to said housing defining said opposed fluid inlets therebetween.

4. The opposed-flow virtual cyclone of claim 3, wherein said plate is constructed of material selected from the group consisting of solid and porous.

5. The opposed-flow virtual cyclone of claim 2, wherein said curved surfaces are of a configuration selected from the group including T-shaped and semicircular.

6. The opposed-flow virtual cyclone of claim 2, additionally including a plate positioned in spaced relation to said opening in said housing opposite said curved surfaces of said housing, for collecting particles passing through said opening in said housing.

7. The opposed-flow virtual cyclone of claim 6, wherein said plate is provided with at least an opening aligned with an axis of said opening in said housing.

8. The opposed-flow virtual cyclone of claim 7, wherein said plate additionally includes a cavity forming member adjacent said opening in said plate.

9. The opposed-flow virtual cyclone of claim 1, in combination with means for collecting particles which are separated, focused, or enriched by said cyclone.

10. The opposed-flow virtual cyclone of claim 9, wherein said means for collecting particles is selected from the group consisting of impingers and impactors.

11. The opposed-flow virtual cyclone of claim 1, wherein an intersection of said fluid inlets and of said fluid outlet are configured to form a particle recirculating region intermediate said fluid inlets and adjacent a point in said fluid outlet where said fluid inlets merge together.

12. The opposed-flow virtual cyclone of claim 11, additionally including means for at least collecting particles from said particle recirculating region.

13. The opposed-flow virtual cyclone of claim 12, wherein said means for at least collecting particles comprises at least a plate located in spaced relation to a terminal end of said fluid outlet.

14. The opposed-flow virtual cyclone of claim 1, wherein said means forming opposed fluid inlets includes a porous member to enable purging of particles from a recirculating region located intermediate said opposed fluid inlets.

15. A device for collecting, classifying, and concentrating particles of a specific size range, comprising:

a pair of virtual cyclones positioned such that a plurality of inlet jets thereof are inwardly directed and symmetrically opposed relative to a plane of symmetry located midway between inlet openings thereof.

16. The device of claim 15, wherein said inlet openings are formed intermediate a housing and a plate member, said housing including a opening therein having an axis defining said plane of symmetry.

17. The device of claim 16, wherein said housing includes curved surfaces along which said inlet jets flow toward said plane of symmetry.

18. The device of claim 17, additionally including a particle recirculating region located intermediate said housing and said plate, about said plane of symmetry, intermediate said inlet jets, and above a point at which said inlet jets merge in said opening of said housing.

19. The device of claim 18, additionally including means for collecting particles from said particle recirculating region.

20. The device of claim 16, wherein said plate member is composed of porous material to enable purging of collected particles.

21. The device of claim 15, wherein said specific size range of said particles is about 1–5 $\mu$m.

22. A method for collecting, classifying, and concentrating particles of a specific size range, comprising, providing a plurality of virtual cyclones positioned such that the inlet jets are inwardly directed and symmetrically opposed relative to a plane of symmetry located midway between the inlet jets, and supplying a fluid to the plurality of virtual cyclones.

* * * * *